(12) United States Patent
Nichols et al.

(10) Patent No.: US 11,023,946 B2
(45) Date of Patent: Jun. 1, 2021

(54) SOCIAL MEDIA HEALTHCARE ANALYTICS

(71) Applicant: OPTUM, INC., Minnetonka, MN (US)

(72) Inventors: Matthew Nichols, Buffalo, MN (US); Genesis Christiansen, Lakeville, MN (US); David Sam, Eden Prairie, MN (US); Benjamin Bublitz, Eden Prairie, MN (US); Jesen Surjadi, Minnetonka, MN (US); Mushir Ahmed Basheer, Eden Prairie, MN (US)

(73) Assignee: OPTUM, INC.

( * ) Notice: Subject to any disclaimer, the term of this patent is extended or adjusted under 35 U.S.C. 154(b) by 1106 days.

(21) Appl. No.: 14/665,596

(22) Filed: Mar. 23, 2015

(65) Prior Publication Data

US 2016/0284037 A1      Sep. 29, 2016

(51) Int. Cl.
*G06Q 50/22*   (2018.01)
*G06Q 30/06*   (2012.01)
*G06Q 30/02*   (2012.01)
*G06Q 50/00*   (2012.01)
*G16H 10/60*   (2018.01)

(52) U.S. Cl.
CPC ..... *G06Q 30/0631* (2013.01); *G06Q 30/0203* (2013.01); *G06Q 50/01* (2013.01); *G16H 10/60* (2018.01)

(58) Field of Classification Search
CPC .... G06Q 50/22; G06Q 50/01; G06Q 30/0203; G06Q 30/0631; G06Q 30/0277; G06Q 30/0207
See application file for complete search history.

(56) References Cited

U.S. PATENT DOCUMENTS 9,508,082 B1 *   11/2016   Mannix   ............. G06Q 30/0201
2014/0121540 A1 *   5/2014   Raskin   ................ A61B 5/6898
                                                                                600/479

(Continued)

OTHER PUBLICATIONS

Greaves et al. ("Harnessing the cloud of patient experience: using social media to detect poor quality healthcare", BMJ Quality & Safety; London vol. 22, Iss. 3, (Mar. 2013): 251. DOI:10.1136/bmjqs-2012-001527) (Year: 2013).*

*Primary Examiner* — Jonathan Durant
*Assistant Examiner* — Chad A Newton
(74) *Attorney, Agent, or Firm* — Seyfarth Shaw LLP; Brian Michaelis

(57) ABSTRACT

A health information system includes a health information data storage machine and a healthcare analytics processor configured to extract healthcare related commentary of healthcare consumers from a social media data storage machine and match portions of the healthcare related commentary to health information of the social media commentators in a combined health information data source. The healthcare analytics processor identifies relationships between consumer sentiment expressed in the social media information and consumer experiences, product usage, diagnoses and outcomes recorded in the health information. Benchmarks and measures of healthcare outcomes and treatments are generated based on matching consumer commentary and consumer sentiments with corresponding indications of actual healthcare experiences of the commentator recorded in the health information.

26 Claims, 5 Drawing Sheets

(56) References Cited

U.S. PATENT DOCUMENTS

| | | | |
|---|---|---|---|
| 2014/0173642 A1* | 6/2014 | Vinson | G06Q 50/01 |
| | | | 725/9 |
| 2014/0316793 A1* | 10/2014 | Pruit | G16H 10/20 |
| | | | 705/2 |
| 2015/0120383 A1* | 4/2015 | Bennah | G06Q 30/0202 |
| | | | 705/7.31 |
| 2015/0302478 A1* | 10/2015 | Michael | G06Q 30/0257 |
| | | | 705/14.55 |
| 2015/0379527 A1* | 12/2015 | Skiba | G06Q 30/0201 |
| | | | 705/7.29 |
| 2016/0082348 A1* | 3/2016 | Kehoe | G06Q 10/101 |
| | | | 463/31 |
| 2016/0196561 A1* | 7/2016 | Iyer | G06Q 30/016 |
| | | | 705/304 |
| 2017/0061102 A1* | 3/2017 | Weber | G06Q 50/01 |
| 2018/0181966 A1* | 6/2018 | Rao | G06Q 30/01 |

* cited by examiner

SOCIAL MEDIA HEALTHCARE ANALYTICS

FIELD OF TECHNOLOGY

The present disclosure is in the field of information technology and more particularly in the field of healthcare data analytics.

BACKGROUND

Healthcare providers, healthcare payers and other healthcare industry stakeholders have access to an increasing amount of information about individual healthcare consumers and various populations and demographic groups. Electronic medical records are commonly used by healthcare providers to store patient health information. Various other forms of patient health information may be stored in various databases and formats by healthcare payers and healthcare providers. Electronic health records and electronic health information exchange are commonly used to securely share electronically stored patient health information among healthcare providers and healthcare payers and consumers. Secure, timely sharing of patient information through electronic health information exchanges can better inform decision making at the points of care and allows providers to improve diagnoses and to avoid readmissions, medication errors and duplicate testing, for example. Different healthcare industry stakeholders may operate and maintain their own secure health information storage systems and machines or may communicate with other healthcare industry stakeholders via health information exchanges or other mechanisms to access patient health information and population health information. A network of two or more health industry stakeholders, such as healthcare providers, healthcare payers and other health data sources in secure communication with each other via a health information exchange is referred to herein as a health information exchange network.

Various standards, policies and technologies for implementing health information exchange are currently available or under development to enable the secure exchange of health information over the Internet. Data that has been standardized for electronic health information exchange may be seamlessly integrated into a recipients' electronic medical records, for example. Even though a vast amount of health information is stored electronically, analyzing the information to improve health care delivery generally involves extensive efforts to identify appropriate data sources and to secure access to the data sources.

SUMMARY

Healthcare industry stakeholders including various health care payers and health care providers commonly advertise on social media platforms such as Facebook and Twitter as well as more traditional media platforms such as broadcast media, print media, and portal advertising. Various techniques have previously implemented for tracking the effectiveness of advertising campaigns by monitoring expressions of consumer sentiments on social media platforms.

Aspects of the present disclosure allow expressions of consumer sentiment by a social media commentator to be matched with health information of the commentator. By matching consumer sentiment to health information, relationships may be identified between consumer sentiment and consumer experiences, product usage, diagnosis and outcomes. Aspects of the present disclosure match social media data healthcare data to track product usage, healthcare outcomes and consumer sentiment. According to aspects of the present disclosure, measures of product usage, healthcare outcomes and consumer sentiment may be generated in real-time and used to evaluate the effectiveness of advertising campaigns, for example.

When consumers receive health care products and/or services from various healthcare organizations, data is generated that describes aspects of the consumer experience, such as physician encounters, clinical treatment information, diagnosis, outcomes, pharmaceutical claims and other medical claims, for example. According to aspects of the present disclosure, analytics match and report information that connects consumer social media commentary and advertising campaigns to each other and to related clinical information and claims information. Matching social media commentary and advertising to clinical information and claims information according to aspects of the present disclosure, provides a new level of insight and opportunity that may help healthcare organizations to manage consumer satisfaction, sales, and outcomes.

Additional features and advantages of the present disclosure are described below. It should be appreciated by those skilled in the art that this disclosure may be readily utilized as a basis for modifying or designing other structures, systems and processes for carrying out the same purposes of the present disclosure. It should also be realized by those skilled in the art that such equivalent implementations do not depart from the teachings of the disclosure as set forth in the appended claims. The novel features, which are believed to be characteristic of the disclosure, both as to its organization and method of operation, together with further objects and advantages, will be better understood from the following description when considered in connection with the accompanying figures. It is to be expressly understood, however, that each of the figures is provided for the purpose of illustration and description only and is not intended as a definition of the limits of the present disclosure.

BRIEF DESCRIPTION OF THE DRAWINGS

The particular features and advantages of the present disclosure will be apparent from the detailed description set forth below in conjunction with the drawings in which like reference characters identify corresponding aspects throughout.

DETAILED DESCRIPTION

Figure 1:
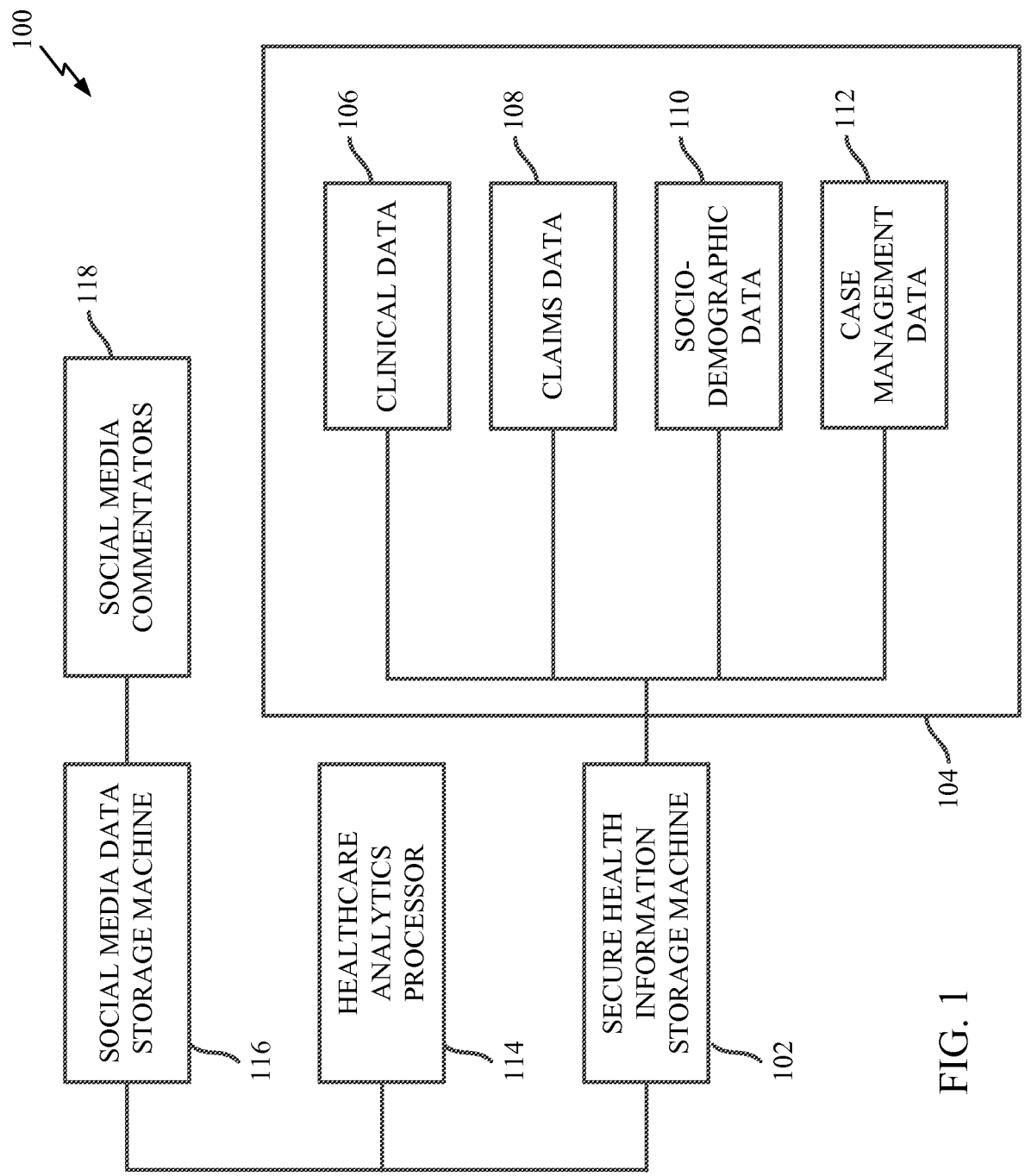
FIG. 1 shows a block diagram of a health information processing system according to an aspect of the present disclosure.

A large amount of consumer healthcare information is routinely collected by healthcare providers, insurance providers, government agencies, researchers and other institutions. According to aspects of the present disclosure, useful compilations of healthcare data are stored in one or more integrated healthcare data warehouses. The healthcare data warehouse may compile healthcare data from various sources and store the compiled data in a useful, secure and appropriately accessible form.

According to aspects of the present disclosure, the compilations of health information may include clinical data for a large number of patients, decades of longitudinal healthcare claim data for a large number of healthcare consumers, and various socio-demographic and care management data, for example.

Clinical data, prescription medication records, claims data, socio-demographic data and care management data may be integrated into the compilations of health information to provide both retrospective and prospective views of healthcare consumers and healthcare consumer populations. This enables healthcare providers to identify at-risk patients earlier, preserve patient health, reduce costs and prevent complications, for example.

Social media platforms are increasingly popular means of electronic communication that enable individuals to instantly publish text and multimedia information to a wide audience. Social media platforms such as Facebook.com and Twitter.com receive, publish and store a large amount of information about social users including commentary published by individual users, and other demographic information about the users.

Information published on social media platforms includes a vast amount of commentary and other inputs expressing the personal sentiments of social media users. Much of the information that is published on social media platforms may be accessed for consumer research and marketing purposes. Marketing researchers may be particularly interested in published expressions of consumer sentiments with regard to certain products or services. For example, information published on social media may be analyzed to evaluate the effects of certain advertising campaigns or other marketing efforts on consumer sentiment. Although information published on social media platforms may provide valuable insights into consumer sentiment, it has heretofore been difficult or impossible to relate consumer expressions of sentiment with actual consumer experiences.

Aspects of the present disclosure tie social media information to healthcare information from various data sets in a claims data, electronic medical records and other clinical and pharmaceutical information to generate a more complete holistic view of the patient. The holistic view of the patient may include information that characterizes the healthcare consumer's sentiments based on their expressions published on social media as well as information from their health records characterizing their actual conditions, behavior, treatments and outcomes.

FIG. 1 illustrates an example of a health information processing system 100 according to an aspect of the present disclosure. The health information processing system 100 including a secure health information data storage machine 102 coupled to a health information exchange network 104. The health information exchange network may include one or more clinical data sources 106 such as healthcare providers, claims data sources 108 such as healthcare payers, socio demographic data sources 110 and case management data sources 112, for example. The secure health information data storage machine 102 stores a compilation of health information and health claims information received from the health information exchange network 104. The health information may be received from electronic medical records of a numerous healthcare consumers via the health information exchange network 104, for example.

The health information processing system 102 also includes a healthcare analytics processor 114 coupled to the secure health data storage machine 102 and coupled to a social media data storage machine 116 of a social media platform. The social media data storage machine 116 stores a compilation of consumer sentiment information received from numerous social media commentators 118.

According to aspects of the present disclosure, the healthcare analytics processor 114 is configured to identify portions of the consumer sentiment information that reference one or more healthcare products or services and match the referenced healthcare products or services to portions of the health information. The healthcare analytics processor is further configured to generate a consumer sentiment characterization of the referenced healthcare products or services based on the portions of the consumer sentiment information matched to the portions of the health information and store the consumer sentiment characterization in the secure health information data storage machine in association with a corresponding healthcare product or service. The compilation of consumer sentiment information may include expressions of consumer need or desire for one or more of the healthcare products or services.

The healthcare analytics processor 114 may be configured to identify the group of social media posters as a potential market for one or more healthcare products/and or services based on their expressions of need or desire, for example. In another example, the healthcare analytics processor 114 may be configured to define a potential market for one or more of the healthcare products or services by identifying a group of the social media commentators in which each member of the group has communicated an expression of favorable sentiment with respect to the one or more related healthcare brands. The healthcare analytics processor 114 may also be configured to identify a trend of increasing or decreasing expressions of similar sentiment associated with one or more of the healthcare products in the consumer sentiment information, for example.

According to another aspect of the present disclosure, the healthcare analytics processor 114 may also be configured to identify social media commentators who have been exposed to one or more particular advertisements and compute a correlation between the consumer sentiment characterization and the identified commentators who have been exposed to the one or more particular advertisements. The healthcare analytics processor 114 may also be configured to identify one or more of the social media commentators as healthcare consumers of one or more health care products or services and match portions of the consumer sentiment information received from the identified social media commentators to the one or more health care products or services.

The healthcare analytics processor 114 may also be further configured to estimate an amount of social media usage by one or more of the social media commentators based on the compilation of consumer sentiment information and identify a correlation between the estimated amount of social media usage and the consumer sentiment characterization for followers of that commentator. The healthcare analytics processor 114 may also be configured to estimate an amount of usage of the one or more healthcare products or services by one or more of the social media commentators based on the compilation of health information and compute a correlation between the estimated amount of usage of the one or more healthcare products or services and the consumer sentiment characterization, for example.

According to another aspect of the present disclosure, the healthcare analytics processor 114 may be configured to compute a benchmark of consumer sentiment for one or more of the healthcare products or services by geographic region or other consumer demographic dimensions based on the stored characterization of consumer sentiment. The healthcare analytics processor 114 may also be configured to generate a user interface dashboard displaying one or more relationships between the consumer sentiment characterization and a portion of the compilation of health information and claims information.

The secure health information storage machine 102 may include one or more data storage computers which may be located in a secure location or may be distributed over a number of secure locations. The secure health information storage machine may also include means for protecting data privacy and security such as means for encryption and secure communication, for example.

Figure 2:
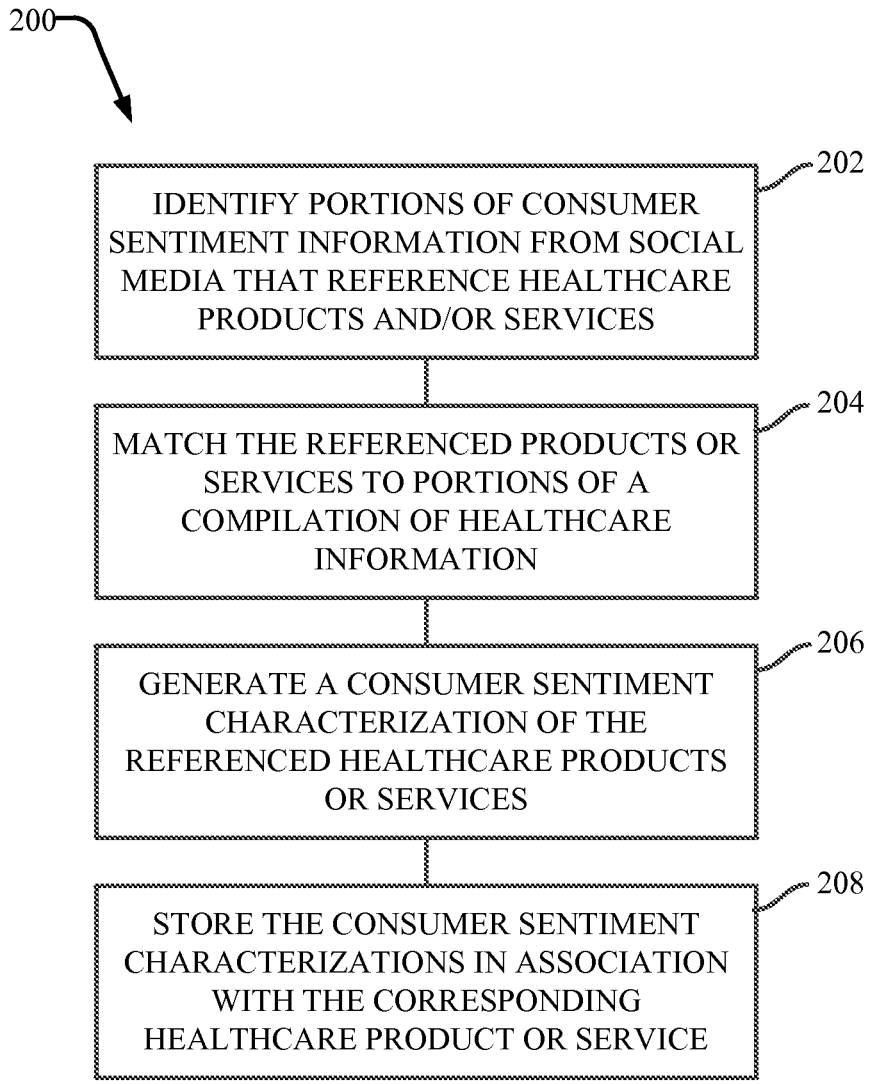
FIG. 2 is a process flow diagram illustrating a health information analytics process according to an aspect of the present disclosure.

A health information analytic process 200 performed by a healthcare analytics processor coupled to a secure health data storage machine and coupled to a social media data storage machine of a social media platform according to an aspect of the present disclosure is described with reference to FIG. 2. According to this aspect of the present disclosure, the social media data storage machine stores a compilation of consumer sentiment information received from a number of social media commentators and the secure health information data storage machine is coupled to a health information exchange network. The secure health information data storage machine stores a compilation of health claims information and health information received from electronic medical records of a plurality of healthcare consumers via the health information exchange network.

At block 202, the process includes, identifying portions of the consumer sentiment information that reference one or more healthcare products or services. At block 204, the process includes matching the referenced healthcare products or services to portions of the health information. At block 206, the process includes generating a consumer sentiment characterization of the referenced healthcare products or services based on the portions of the consumer sentiment information matched to the portions of the health information. And at block 208, the process includes storing the consumer sentiment characterization in the secure health information data storage machine in association with a corresponding healthcare product or service.

The process 200 may also include identifying one or more of the plurality of social media commentators as being included in the plurality of healthcare consumers, and matching portions of the consumer sentiment information received from the identified social media commentators to the one or more health care products or services. In another example, the process 200 may include defining a potential market for one or more of the healthcare products or services by identify a group of the social media commentators in which each member of the group has communicated an expression of favorable sentiment with respect to the one or more healthcare products or services.

In another example, the process 200 may include identifying the group of social media posters as a potential market for one or more healthcare products and/or services based on their expressions of need or desire included in the compilation of consumer sentiment information. The process 200 may further include identifying a trend of increasing or decreasing expressions of similar sentiment associated with one or more of the healthcare products in the consumer sentiment information.

According to an aspect of the present disclosure, the process 200 may include estimating an amount of social media usage by one or more of the social media commentators based on the compilation of consumer sentiment information and identifying a correlation between the estimated amount of social media usage and the consumer sentiment characterization. In another example, the process 200 may include estimating an amount of usage of one or more healthcare products or services by one or more of the social media commentators based on the compilation of health information and computing a correlation between the estimated amount of usage of the one or more healthcare products or services and the consumer sentiment characterization.

According to another aspect of the present disclosure, the process 200 may include identifying commentators in the plurality of social media commentators who have been exposed to one or more particular advertisements and computing a correlation between the consumer sentiment characterization and the identified commentators who have been exposed to the one or more particular advertisements and/or computing a benchmark of consumer sentiment for one or more of the healthcare products or services base on the stored characterization of consumer sentiment. In another example, the process 200 may include generating a user interface dashboard displaying one or more relationships between the consumer sentiment characterization and a portion of the compilation of health information and claims information.

Figure 3:
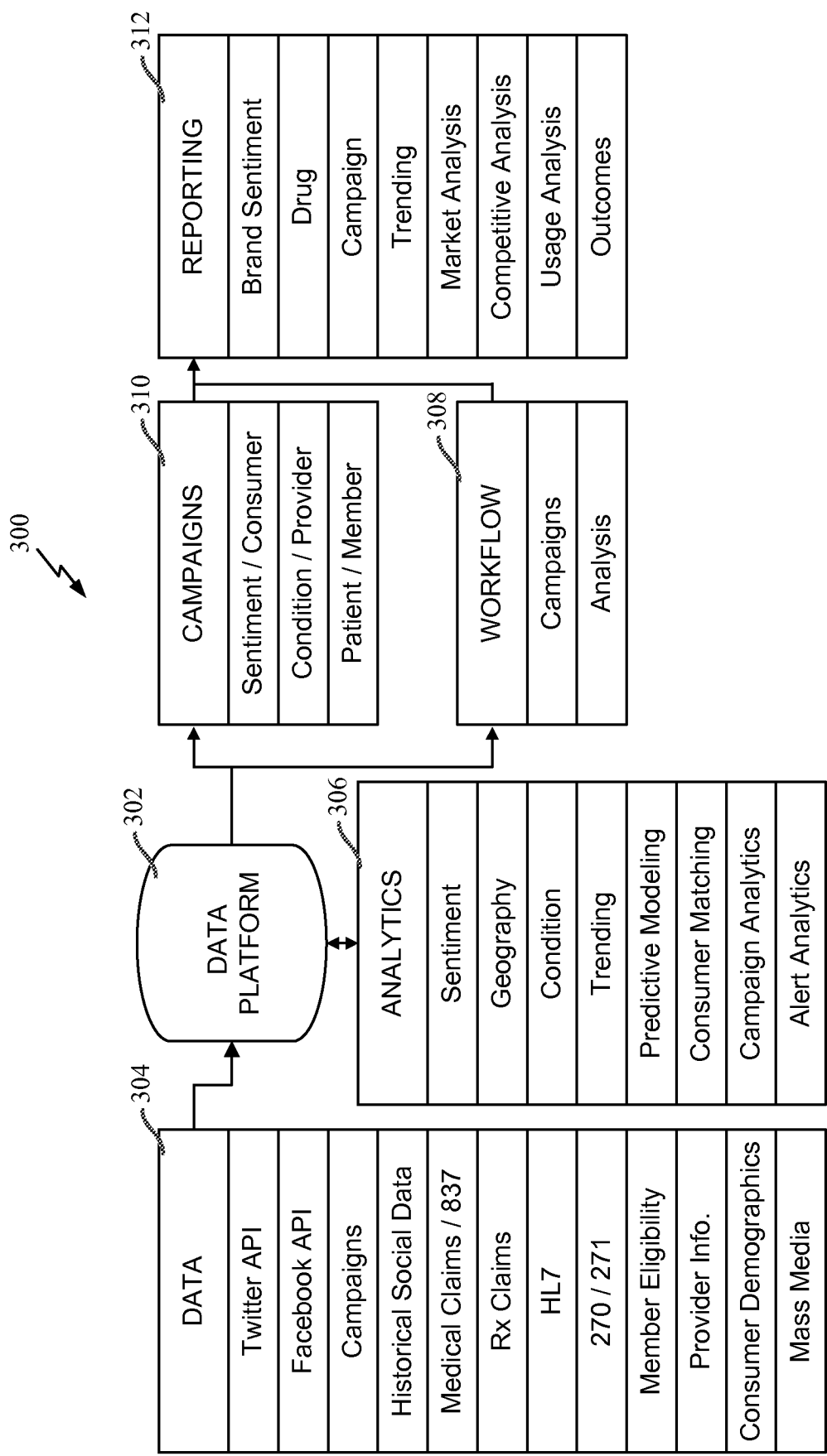
FIG. 3 is a block diagram illustrating a health information analytics process according to an aspect of the present disclosure.

Referring to FIG. 3, a system 300 for processing healthcare data according to aspects of the present disclosure includes a data platform 302, that accesses data from a variety of different data sources 304. The data sources may include application programming interfaces (APIs) to social media platforms, such as the well-known Twitter and Facebook social media platforms, historical social data, healthcare insurance claims, healthcare insurance membership databases, electronic medical records, health information exchange sources, healthcare provider databases, consumer demographic databases and/or mass media information sources, for example. The data platform 302 provides an analytics engine 306 configured to extract, correlate and/or compile desired information from the variety of different data sources 304. The analytics engine may be configured to automatically generate sentiment information related to particular healthcare companies, products or services, for example, and to perform trend analysis, predictive modeling consumer matching campaign analytics and/or alert analytics based on the combination of different data sources 304. The analytics engine 306 may be used to generate or facilitate workflows 308, such as campaigns and/or analysis workflows. For example, campaigns 310 may be generated based on matching of sentiment information to consumer information, condition information to providers or patient information to health insurance member information, for example. The system 300 is configured to automatically generate reports 312 such as brand sentiment reports, drug reports, campaign reports, trending reports, market analysis reports, competitive analysis reports, usage analysis reports and outcome reports, for example.

Combining expressions published on one or more social media platforms by a healthcare consumer with health information of the consumer according to aspects of the present disclosure provides a holistic view of the healthcare consumer, including their activities, their care and their healthcare outcomes.

In one example, according to an aspect of the present disclosure, matching a social media commentator to their healthcare information may be performed by receiving the name, address, date of birth and/or other demographic information of the social media commentators from the social media platform. Social media information may also include dates or times or approximate dates and times and/or locations of a healthcare service or healthcare product purchase or service experienced by the social media commentator. This additional information may be compared with health information stored in a healthcare data storage machine to identify the social media commentator as a particular healthcare consumer whose health information is included in a compilation of clinical health information and/or health claims information stored in the healthcare data storage machine. The clinical health information and/or health claims information may associate a unique identification number with the healthcare consumer which may then be associated with the healthcare commentator for matching social media comments with the compilation of health information.

Once a healthcare consumer is identified in the various data sets then the comments and sentiments of the healthcare consumer may be compared with particular events, experiences, treatments, conditions and/or outcomes of the healthcare consumer. Commentators who have published comments about a certain healthcare product or service on a social media platform may be identified globally, or in a certain geographical region, for example. According to aspects of the present disclosure, a compilation of clinical health information and/or healthcare claims information may be accessed to determine the amount of actual experience that particular commentators have with the healthcare products or services that they comment upon.

In one example, if a healthcare consumer publishes comments on social media about a particular medication, the healthcare consumer's clinical health information may be accessed to determine how the medication may have been used by the healthcare consumer and how it may have affected the healthcare consumer. The healthcare consumer's lab results, which may be included in the clinical health information may indicate whether the healthcare consumer is in compliance or out of compliance with the key measures related to the particular medication, for example.

The combined health information and social media information may be used to monitor the effectiveness of advertising campaigns with respect to changes in consumer sentiment, to target where advertising campaigns should be launched based on the actual use of the advertised healthcare products or services.

The social media commentary may be responsive to particular events, advertisements, or campaigns or may include general expressions of sentiment with respect to a healthcare product or service. In addition to expressions of consumer sentiment, the social media commentary may include information related to the commentators experience with a healthcare product, pharmaceutical company, healthcare provider and/or healthcare payer, for example.

Aspects of the present disclosure tie social media commentary and other information received from a social media platform to a vast amount of health information from electronic health records, health information networks and healthcare claims information to manage healthcare, healthcare engagement, and healthcare effectiveness.

Aspects of the present disclosure provide real-time access or rapid access to healthcare related information extracted from social media publications of healthcare consumers. This real-time nature of social media data adds value compared to many other health information sources such as claims data or clinical data which may take weeks or months to reach the health information data storage machine. In one example, real-time health information from social media commentators may be used to track a flu outbreak or outbreaks of other contagious conditions in various regions. The inclusion of real-time health information adds value to other compilations compilation of health information and facilitates more timely and effective responses to health related events.

The disclosed health information analytics process involves retrieving social media information from special purpose machines in the field of social media information technology applying novel insights and specific techniques to identify healthcare related information within the social media information in real-time, match the identified information with healthcare information from a combination of health information data sources on another special purpose machine in the unrelated field of health information technology. The disclosed special purpose health information storage machine and healthcare analytics processor ties the inventive concepts to particular machines and transforms information in improved, non-routine and useful manner.

Aspects of the present disclosure improve the particular technical environment of health information technology by extracting health related information from social media machines in real time and performing innovative techniques for matching the health information to particular medical records, for example. Aspects of the present disclosure improve the operation of certain health information dashboards, machines, networks and/or systems by generating a compilation of health information including real-time representations of healthcare consumers, thereby improving the quality of available health information, improving patient care, and reducing healthcare costs. Certain aspects of the present disclosure are confined to the field of health information technology, in which they provide substantial improvement and technological innovation.

In various embodiments, software may be stored in a computer program product and loaded into a special purpose computer system using removable storage drive, hard disk drive or communications interface. Aspects of the disclosed process may be implemented in control logic or computer program instructions, which when executed cause the special purpose computer system to perform the functions of various embodiments as described herein. Implementation of systems including special purpose machines to perform the functions described herein will be apparent to persons skilled in the relevant art(s).

A method of mining healthcare information from commentary published on a social media platform according to an aspect of the present disclosure includes extracting portions of consumer sentiment information that reference one or more healthcare companies, products or services from a plurality of comments published by one or more social media commentators on the social media platform. The method also includes extracting portions of health information that reference one or more of the healthcare companies, products or services from a compilation of healthcare provider information and healthcare insurance claims information. According to this aspect of the present disclosure, the method includes automatically matching the portions of consumer sentiment information to portions of the health information based on the referenced healthcare companies, products or services, automatically generating a consumer sentiment characterization of the referenced healthcare companies, products or services based on the portions of the consumer sentiment information. The method also includes storing the consumer sentiment characterization in association with a corresponding healthcare company, product or service.

According to an aspect of the present disclosure, the method includes automatically generating the consumer sentiment characterization based on the portions of consumer sentiment information published by a first commentator in the one or more social media commentators, automatically extracting an indication of the first commentator's experience involving the one or more healthcare companies, products or services from the compilation of health information, and automatically computing a correlation between the indication of the first commentator's experience and the consumer sentiment characterization.

According to another aspect of the present disclosure, the method includes automatically generating the consumer sentiment characterization based on the portions of consumer sentiment information published by one or more social media followers of a first commentator in the one or more social media commentators, and automatically identifying a correlation between the one or more social media followers of first commentator and the consumer sentiment characterization.

Figure 4:
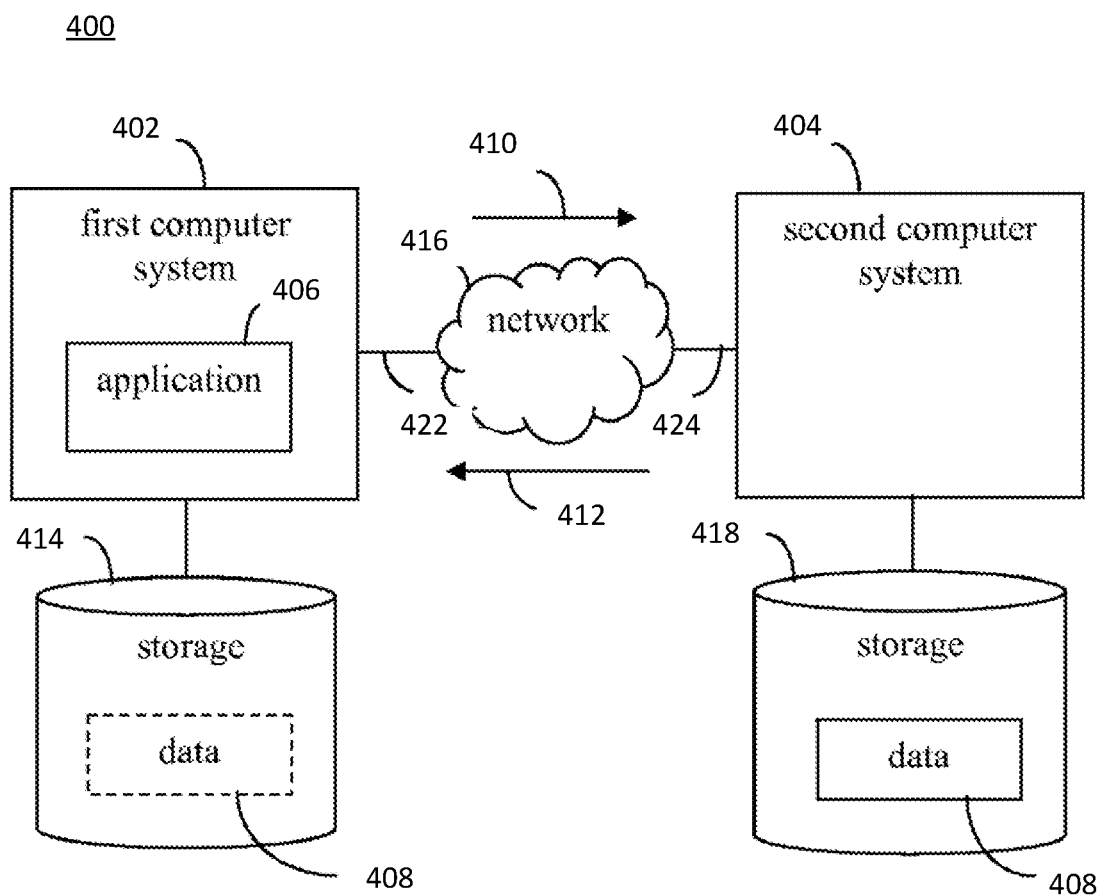
FIG. 4 shows a block diagram of a data communication system for mining healthcare information from commentary published on a social media platform according to aspects of the present disclosure.

Aspects of the present disclosure relate to data communications in distributed systems. For example, FIG. 4 shows a block diagram of a data communication system 400, according to an example embodiment. As shown in FIG. 4, system 400 includes a first computer system 402, a second computer system 404, a first storage 414, a network 416, and a second storage 418. An application 406 executes in first computer system 402. Storage 414 is coupled to first computer system 402. Storage 418 is coupled to second computer system 404. First and second computer systems 402 and 404 are communicatively coupled by network 416. System 400 is configured to enable resources to be transferred between first and second computer systems 402 and 404.

First and second computer systems 402 and 404 may each be any type of computing device, including a desktop computer (e.g., a personal computer), a server, a mobile computer or computing device such as a smart phone or tablet computer device, a personal digital assistant (PDA), a laptop computer, a notebook computer, etc., or other type of computer system. Storage 414 and storage 418 may each include one or more of any type of storage mechanism to store content (e.g., objects), including a hard disk drive, an optical disc drive, a memory device such as a RAM device, a ROM device, etc., and/or any other suitable type of storage medium.

Network 416 may include one or more communication links and/or communication networks, such as a LAN (local area network), a WAN (wide area network), or a combination of networks, such as the Internet. First and second communication links 422 and 424, which respectively couple first and second computer systems 402 and 404 to network 416, may include any number of communication links, including wired and/or wireless links, such as IEEE 802.11 wireless LAN (WLAN) wireless links, Worldwide Interoperability for Microwave Access (Wi-MAX) links, cellular network links, wireless personal area network (PAN) links (e.g., Bluetooth™ links), Ethernet links, USB links, etc.

Application 406 may issue a query for a resource (e.g., data). The resource may be accessible as data 408 contained in storage 418 at second computer system 404. To obtain the resource, first computer system 402 may transmit the query from first computer system 402 in a first communication signal 410. For example, first computer system 402 may contain an agent (e.g., a "client" agent) configured to handle transmission of queries. First communication signal 410 is transmitted through a first communication link 422, network 416, and a second communication link 424, and is received by second computer system 404. First communication signal 410 may be transmitted in any form, including in the form of a stream of packets (e.g., IP packets).

Second computer system 404 processes the request received in first communication signal 410. For example, second computer system 404 may include an agent (e.g., a "server" agent) configured to process received queries. Second computer system 404 retrieves data 408 from storage 418, which may contain a database or other data source. Second computer system 404 generates a second communication signal 412, which is a response signal that includes data 408. Second communication signal 412 is transmitted through second communication link 424, network 416, and first communication link 422, and is received by first computer system 402. Application 406 receives data 408 included in second communication signal 412, which may be stored in storage 414 (as indicated by dotted lines in FIG. 4). Second communication signal 412 may be transmitted in any form, including in the form of a stream of packets (e.g., IP packets).

Currently, applications and services are being developed that include the use of REST (representational state transfer) interfaces for accessing resources and a URI (Uniform Resource Identifier) namespace that identifies the resources. These applications and services enable web-based data sources to be accessed in a more efficient manner. For example, second computer system 404 in FIG. 4 may be configured to have a REST interface to enable data 408 to be accessed according a URI.

Figure 5:
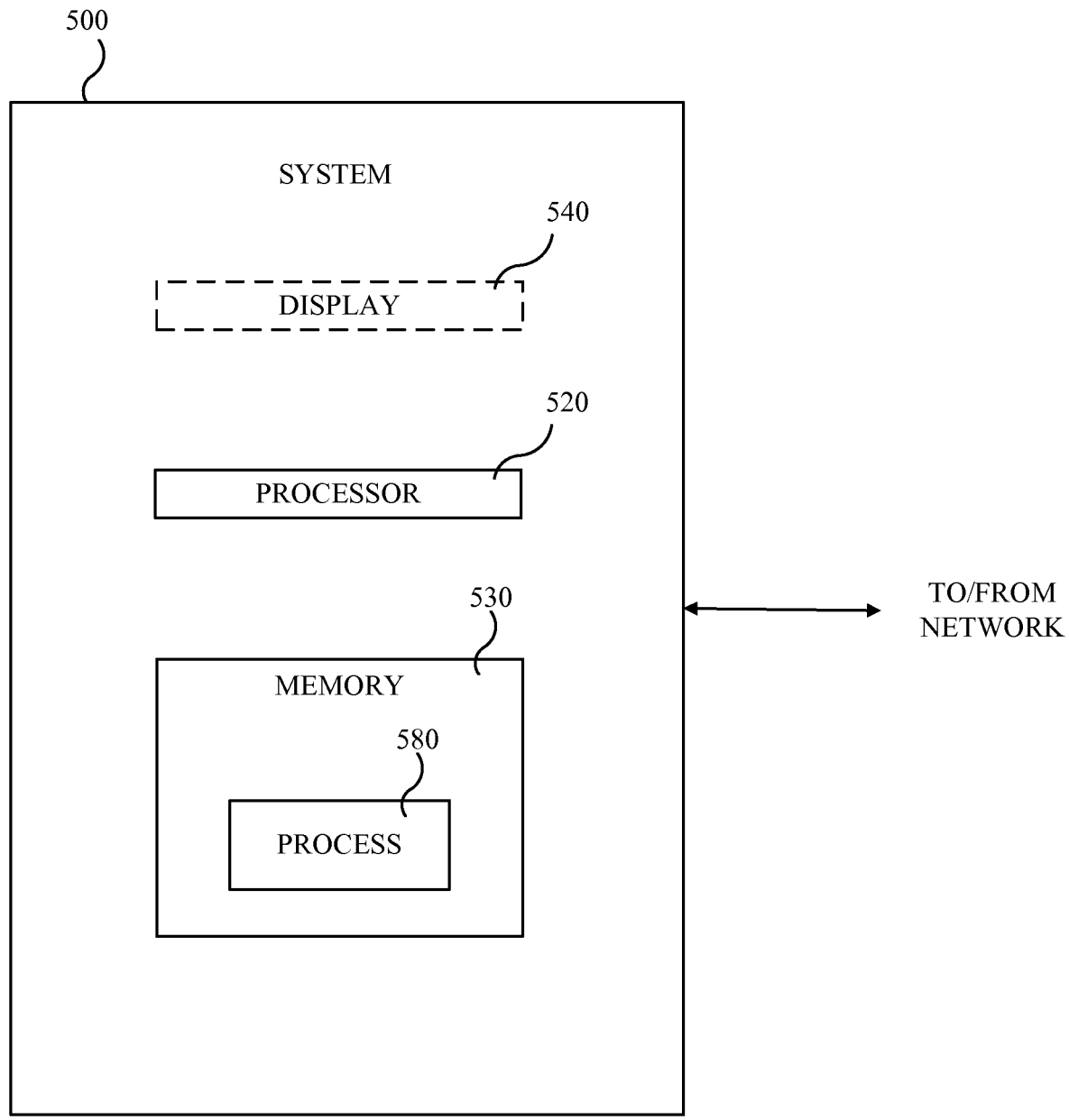
FIG. 5 is a block diagram of a system that can implement part or all of one or more aspects or processes of systems for mining healthcare information from commentary published on a social media platform according to embodiments of the present disclosure.

FIG. 5 is a block diagram of a system 500 that can implement part or all of one or more aspects or processes of systems within which a web-native bridge according to embodiments of the present disclosure can operate or within which methods according to embodiments of the present disclosure can be carried out. As shown in FIG. 5, memory 530 configures the processor 520 to implement one or more aspects of the methods, steps, and functions disclosed herein (collectively, shown as process 580 in FIG. 5). Different method steps can be performed by different processors. The memory 530 could be distributed or local and the processor 520 could be distributed or singular. The memory 530 could be implemented as an electrical, magnetic or optical memory, or any combination of these or other types of storage devices. It should be noted that if distributed processors are employed, each distributed processor that makes up processor 520 generally contains its own addressable memory space. It should also be noted that some or all of computer system 500 can be incorporated into an application-specific or general-use integrated circuit. For example, one or more method steps could be implemented in hardware in an ASIC rather than using firmware. Display 540 is representative of a variety of possible input/output devices (e.g., displays, touchscreens, mice, keyboards, and so on).

According to an aspect of the present disclosure, a system for mining healthcare information from commentary published on a social media platform includes one or more electronic data storage systems such as storage 414, 418 shown in FIG. 4, for example, one or more processors such as processor 522 shown in FIG. 5, for example, in communication with the electronic data storage systems, and a user interface in communication with the processor. The user interface may include a display in communication with the processor and an input device in communication with the processor, for example. According to this aspect of the present disclosure, the processors are configured to automatically extract portions of consumer sentiment information that reference one or more healthcare companies, products or services from a plurality of comments published by one or more social media commentators on the social media platform. The processors are also configured to automatically extract portions of health information that reference one or more of the healthcare companies, products or services from a compilation of healthcare provider information and healthcare insurance claims information. The processors are further configured to automatically match the portions of consumer sentiment information to portions of the health information based on the referenced healthcare companies, products or services, and to automatically generate a consumer sentiment characterization of the referenced healthcare companies, products or services based on the portions of the consumer sentiment information. The processors may then store the consumer sentiment characterization in association with a corresponding healthcare company, product or service.

According to another aspect of the present disclosure, the processors are configured to generate the consumer sentiment characterization based on the portions of consumer sentiment information published by a first commentator in the one or more social media commentators, extract an indication of the first commentator's experience involving the one or more healthcare companies, products or services from the compilation of health information, and compute a correlation between the indication of the first commentator's experience and the consumer sentiment characterization. The processors may also be configured to cause the user interface to display a representation of the computed correlation(s).

The systems, machines and processes described herein may be used in association with web services, utility computing, pervasive and individualized computing, security and identity solutions, autonomic computing, cloud computing, commodity computing, mobility and wireless solutions, open source, biometrics, grid computing and/or mesh computing.

Databases discussed herein are generally implemented on special purpose machines to ensure privacy of confidential health information and data security is preserved in accordance with industry standards and government regulations. The databases may include relational, hierarchical, graphical, or object-oriented structure and/or other database configurations. Moreover, the databases may be organized in various manners, for example, as data tables or lookup tables. In addition to the inventive techniques for combining health information with social media information disclosed herein, association of certain data may be accomplished through various data association technique such as those known or practiced in the art. One skilled in the art will also appreciate that databases, systems, devices, servers or other components of the disclosed systems or machines may consist of any combination thereof at a single location or at multiple locations, wherein each database, system or machine may include suitable security features, such as firewalls, access codes, encryption, decryption, compression, decompression, and/or the like. The special purpose systems, networks and/or computers discussed herein may provide a suitable website or other Internet-based graphical user interface which is accessible by users.

Functional blocks of the block diagrams and flowchart illustrations support combinations of means for performing the specified functions, combinations of steps for performing the specified functions, and program instruction means for performing the specified functions. It should be understood that each functional block of the block diagrams and flowchart illustrations, and combinations of functional blocks in the block diagrams and flowchart illustrations, can be implemented by either special purpose hardware-based computer systems which perform the specified functions or steps, or suitable combinations of special purpose hardware and computer instructions. It should be further appreciated that the multiple steps as illustrated and described may be combined into single webpages and/or windows but have been expanded for the sake of simplicity. In other cases, steps illustrated and described as single process steps may be separated into multiple webpages and/or windows but have been combined for simplicity.

Benefits, other advantages, and solutions to problems have been described herein with regard to specific embodiments. However, the benefits, advantages, solutions to problems, and any elements that may cause any benefit, advantage, or solution to occur or become more pronounced are not to be construed as critical, required, or essential features or elements of the disclosure. The scope of the disclosure is accordingly to be limited by nothing other than the appended claims, in which reference to an element in the singular is not intended to mean "one and only one" unless explicitly so stated, but rather "one or more".

Although illustrative embodiments of the present disclosure have been described herein with reference to the accompanying drawings, it is to be understood that the present disclosure is not limited to those precise embodiments, and that various other changes and modifications may be made by one skilled in the art without departing from the scope or spirit of the disclosure.

What is claimed is:

1. A health information processing system, comprising:
a secure health information data storage machine coupled to a health information exchange network including at least one clinical data source, at least one claims data source, at least one socio demographic data source, and at least one case management data source, the secure health information data storage machine storing a compilation of health information and health claims information, the health information received from electronic medical records of a plurality of healthcare consumers via the health information exchange network,
a healthcare analytics processor coupled to the secure health data storage machine and coupled to a social media data storage machine of a social media platform, the social media data storage machine storing a compilation of consumer sentiment information extracted by the healthcare analytics processor from social media data from a plurality of social media commentators;
wherein the healthcare analytics processor is configured to:
identify and extract portions of the consumer sentiment information that reference one or more healthcare companies, products or services from the social media data;
match the referenced healthcare companies, products or services from the consumer sentiment information to portions of the health information;

generate a consumer sentiment characterization of the referenced healthcare companies, products or services based on the portions of the consumer sentiment information matched to the portions of the health information;

match one of the social media commentators to his/her electronic medical records from the secure health information data storage machine using the social media data and the health information to identify the social media commentator as one of the plurality of healthcare consumers;

combine the health information received from electronic medical records of the plurality of healthcare consumers and the consumer sentiment information from the social media data of the social media commentators when the electronic medical records are matched to one of the social media commentators;

determine a health experience for each social media commentator based on the combined health information and the consumer sentiment information influencing the consumer sentiment characterization; and store the consumer sentiment characterization in the secure health information data storage machine in association with a corresponding healthcare product or service.

2. The health information processing system of claim 1, wherein the healthcare analytics processor is further configured to:

identify one or more of the plurality of social media commentators as being included in the plurality of healthcare consumers; and match portions of the consumer sentiment information that received from the identified social media commentators to the one or more healthcare companies, products or services.

3. The health information processing system of claim 1, wherein the healthcare analytics processor is further configured to:

define a potential market for one or more of the healthcare companies, products or services by identify a group of the social media commentators in which each member of the group has communicated an expression of favorable sentiment with respect to the one or more healthcare companies, products or services.

4. The health information processing system of claim 1, wherein the compilation of consumer sentiment information includes expressions of consumer need or desire for one or more of the healthcare products or services, and wherein the healthcare analytics processor is further configured to identify the group of social media posters as a potential market for one or more healthcare companies, products/and or services based on their expressions of need or desire.

5. The health information processing system of claim 1, wherein the healthcare analytics processor is further configured to identify a trend of increasing or decreasing expressions of similar sentiment associated with one or more of the healthcare companies, products or services in the consumer sentiment information.

6. The health information processing system of claim 1, wherein the healthcare analytics processor is further configured to estimate an amount of social media usage by one or more of the social media commentators based on the compilation of consumer sentiment information; and identify a correlation between the estimated amount of social media usage and the consumer sentiment characterization.

7. The health information processing system of claim 1, wherein the healthcare analytics processor is further configured to generate the consumer sentiment characterization of the referenced healthcare companies, products or services based on the portions of the consumer sentiment information published by follower of a first social media commentator; and identify a correlation between followers of the commentator and the consumer sentiment characterization.

8. The health information processing system of claim 1, wherein the healthcare analytics processor is further configured to:

estimate an amount of usage of the one or more healthcare companies, products or services by one or more of the social media commentators based on the compilation of health information; and compute a correlation between the estimated amount of usage of the one or more healthcare companies, products or services and the consumer sentiment characterization.

9. The health information processing system of claim 1, wherein the healthcare analytics processor is further configured to:

identify commentators in the plurality of social media commentators who have been exposed to one or more particular advertisements; and compute a correlation between the consumer sentiment characterization and the identified commentators who have been exposed to the one or more particular advertisements.

10. The health information processing system of claim 1, wherein the healthcare analytics processor is further configured to:

compute a benchmark of consumer sentiment for one or more of the healthcare products or services based on the stored characterization of consume sentiment.

11. The health information processing system of claim 1, wherein the healthcare analytics processor is further configured to:

generate a user interface dashboard displaying one or more relationships between the consumer sentiment characterization and a portion of the compilation of health information and claims information.

12. A health information analytic process performed by a healthcare analytics processor coupled to a secure health data storage machine and coupled to a social media data storage machine of a social media platform, the social media data storage machine storing a compilation of consumer sentiment information extracted by the healthcare analytics processor from social media data from a plurality of social media commentators, wherein the secure health information data storage machine is coupled to a health information exchange network including at least one clinical data source, at least one claims data source, at least one socio demographic data source, and at least one case management data source, the secure health information data storage machine storing a compilation of health information and health claims information, the health information received from electronic medical records of a plurality of healthcare consumers via the health information exchange network, the process comprising:

identifying and extracting portions of the consumer sentiment information that reference one or more healthcare companies, products or services from the social media data;

matching the referenced healthcare companies, products or services from the consumer sentiment information to portions of the health information;

generating a consumer sentiment characterization of the referenced healthcare companies, products or services based on the portions of the consumer sentiment information matched to the portions of the health information;

matching one of the social media commentators to his/her electronic medical records from the secure health information data storage machine using the social media data and the health information to identify the social media commentator as one of the plurality of healthcare consumers;

combining the health information received from electronic medical records of the plurality of healthcare consumers and the consumer sentiment information from the social media data of the social media commentators when the electronic medical records are matched to one of the social media commentators;

determining a health experience for the social media commentators based on the combined health information and the consumer sentiment information influencing the consumer sentiment characterization; and storing the consumer sentiment characterization in the secure health information data storage machine in association with a corresponding healthcare companies, products or service.

13. The process of claim 12, further comprising:
identifying one or more of the plurality of social media commentators as being included in the plurality of healthcare consumers; and
matching portions of the consumer sentiment information that received from the identified social media commentators to the one or more healthcare companies, products or services.

14. The process of claim 12, further comprising::
defining a potential market for one or more of the healthcare companies, products or services by identify a group of the social media commentators in which each member of the group has communicated an expression of favorable sentiment with respect to the one or more similar healthcare companies, products or services.

15. The process of claim 12, wherein the compilation of consumer sentiment information includes expressions of consumer need or desire for one or more of the healthcare companies, products or services, and wherein the healthcare analytics processor is further configured to identify the group of social media posters as a potential market for one or more healthcare companies, products or services based on their expressions of need or desire.

16. The process of claim 12, wherein the healthcare analytics processor is further configured to identify a trend of increasing or decreasing expressions of similar sentiment associated with one or more of the healthcare companies, products or services in the consumer sentiment information.

17. The process of claim 12, further comprising:
estimating an amount of social media usage by one or more of the social media commentators based on the compilation of consumer sentiment information; and
identifying a correlation between the estimated amount of social media usage and the consumer sentiment characterization.

18. The process of claim 12, further comprising:
estimating an amount of usage of the one or more healthcare companies, products or services by one or more of the social media commentators based on the compilation of health information; and
computing a correlation between the estimated amount of usage of the one or more healthcare companies, products or services and the consumer sentiment characterization.

19. The process of claim 12, further comprising:
identifying commentators in the plurality of social media commentators who have been exposed to one or more particular advertisements; and
computing a correlation between the consumer sentiment characterization and the identified commentators who have been exposed to the one or more particular advertisements.

20. The process of claim 12, further comprising computing a benchmark of consumer sentiment for one or more of the healthcare companies, products or services base on the stored characterization of consumer sentiment.

21. The process of claim 12, further comprising generating a user interface dashboard displaying one or more relationships between the consumer sentiment characterization and a portion of the compilation of health information and claims information.

22. A method of mining healthcare information from commentary published on a social media platform, the method comprising:
extracting portions of consumer sentiment information that reference one or more healthcare companies, products or services from a plurality of comments from social media data published by one or more social media commentators on the social media platform;
extracting portions of health information that reference one or more of the healthcare companies, products or services from a compilation of healthcare provider information and healthcare insurance claims information, the health information received from electronic medical records of a plurality of healthcare consumers,
automatically matching the portions of consumer sentiment information to portions of the health information based on the referenced healthcare companies, products or services;
automatically generating a consumer sentiment characterization of the referenced healthcare companies, products or services based on the portions of the consumer sentiment information;
matching one of the social media commentators to his/her electronic medical records from the secure health information data storage machine using the social media data and the health information to identify the social media commentator as one of the plurality of healthcare consumers;
combining the health information received from electronic medical records of a plurality of healthcare consumers and the consumer sentiment information from social media commentators when the electronic medical records are matched to one of the social media commentators;
determining a health experience for social media commentators based on the combined health information and the consumer sentiment information influencing the consumer sentiment characterization; and
storing the consumer sentiment characterization in association with a corresponding healthcare company, product or service.

23. The method of claim 22, comprising:
automatically generating the consumer sentiment characterization based on the portions of consumer sentiment information published by a first commentator in the one or more social media commentators;
automatically extracting an indication of the first commentator's experience involving the one or more healthcare companies, products or services from the compilation of health information; and
automatically computing a correlation between the indication of the first commentator's experience and the consumer sentiment characterization.

24. The method of claim 22, further comprising:
automatically generating the consumer sentiment characterization based on the portions of consumer sentiment information published by one or more social media followers of a first commentator in the one or more social media commentators; and
automatically identifying a correlation between the one or more social media followers of first commentator and the consumer sentiment characterization.

25. A system for mining healthcare information from commentary published on a social media platform, the system comprising:
one or more electronic data storage systems;
one or more processors in communication with the electronic data storage systems; and
a user interface in communication with the processor, the user interface comprising a display in communication with the processor and an input device in communication with the processor;
wherein the processors are configured to:
automatically extract portions of consumer sentiment information that reference one or more healthcare companies, products or services from a plurality of social media comments published by one or more social media commentators on the social media platform;
automatically extract portions of health information that reference one or more of the healthcare companies, products or services from a compilation of healthcare provider information and healthcare insurance claims information, the health information received from electronic medical records of a plurality of healthcare consumers,
automatically match the portions of consumer sentiment information to portions of the health information based on the referenced healthcare companies, products or services;
automatically generate a consumer sentiment characterization of the referenced healthcare companies, products or services based on the portions of the consumer sentiment information;
match one of the social media commentators to his/her electronic medical records from the secure health information data storage machine using the social media data and the health information to identify the social media commentator as one of the plurality of healthcare consumers;
combine the health information received from electronic medical records of the plurality of healthcare consumers and the consumer sentiment information from the social media comments of the social media commentators that match one of the plurality of healthcare consumers;
determine a health experience for social media commentators based on the combined health information and the consumer sentiment information influencing the consumer sentiment characterization;
store the consumer sentiment characterization in association with a corresponding healthcare company, product or service; and
identifying a trend of increasing or decreasing consumer sentiment characterizations associated with one or more of the healthcare companies, healthcare products or services in the consumer sentiment information.

26. The system of claim 25, wherein the processors are configured to:
generate the consumer sentiment characterization based on the portions of consumer sentiment information published by a first commentator in the one or more social media commentators;
extract an indication of the first commentator's experience involving the one or more healthcare companies, products or services from the compilation of health information; and
compute a correlation between the indication of the first commentator's experience and the consumer sentiment characterization.

* * * * *